United States Patent
Khorshid

(10) Patent No.: US 10,624,927 B2
(45) Date of Patent: Apr. 21, 2020

(54) SEPARATION AND FORMULATION OF BIOACTIVE FRACTION AND SUBFRACTION FROM CAMEL URINE WORKS AS ANTICANCER AGENT

(71) Applicant: Fatin A. Khorshid, Jeddah (SA)

(72) Inventor: Fatin A. Khorshid, Jeddah (SA)

( * ) Notice: Subject to any disclaimer, the term of this patent is extended or adjusted under 35 U.S.C. 154(b) by 0 days.

(21) Appl. No.: 16/047,620

(22) Filed: Jul. 27, 2018

(65) Prior Publication Data

US 2019/0008901 A1 Jan. 10, 2019

Related U.S. Application Data

(62) Division of application No. 12/178,152, filed on Jul. 23, 2008, now abandoned.

(51) Int. Cl.
*A61K 35/22* (2015.01)
*A61K 47/46* (2006.01)

(52) U.S. Cl.
CPC .............. *A61K 35/22* (2013.01); *A61K 47/46* (2013.01)

(58) Field of Classification Search
None
See application file for complete search history.

(56) References Cited

U.S. PATENT DOCUMENTS 6,896,907 B2 * 5/2005 Khanuja ................ A61K 35/22
424/537

FOREIGN PATENT DOCUMENTS

WO WO 2012/019295 * 2/2012

OTHER PUBLICATIONS

Al-Harbi et al. "Effect of camel urine on the cytological and biochemical changes induced by cyclophosphamide in mice" Journal of Ethnopharmacology 52 (1996) 129-137 (Year: 1996).*
Al-Yousef et al. "Camel urinecomponentsdisplayanti-cancerproperties in vitro" Journal of Ethnopharmacology 143(2012)819-825 (Year: 2012).*
American Cancer Society "How Chemotherapy Drugs Work" 6 pgs 2016 (Year: 2016).*
American Cancer Society "How Is Chemotherapy Used to Treat Cancer" 5 pgs 2016 (Year: 2016).*
Gillet 2011 "Redefining the relevance of established cancer cell lines to the study of mechanisms of clinical anti-cancer drug resistance" 18708-187131 | PNAS | Nov. 15, 2011 | vol. 108 | No. 46 (Year: 2011).*
Gillet 2013 "The Clinical Relevance of Cancer Cell Lines" J Natl Cancer Inst;2013;105:452-458 (Year: 2013).*
Mak et al. "Lost in translation: animal models and clinical trials in cancer treatment" Am J Transl Res 2014;6(2):114-118 (Year: 2014).*

* cited by examiner

*Primary Examiner* — Thane Underdahl
(74) *Attorney, Agent, or Firm* — Abelman, Frayne & Schwab

(57) ABSTRACT

A pharmaceutical composition includes an effective amount of a bio-active fraction or subfraction of lyophilized camel urine. The composition is used as an anti-cancer drug which selectively targets the cancer cells without affecting the normal cells.

7 Claims, 10 Drawing Sheets

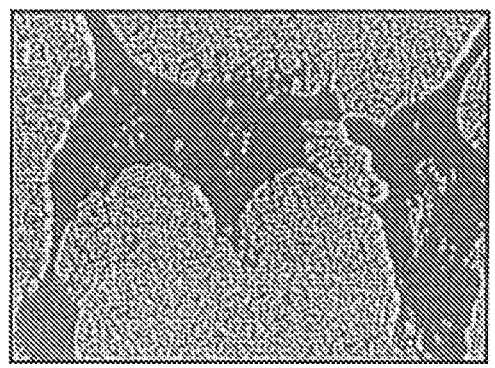 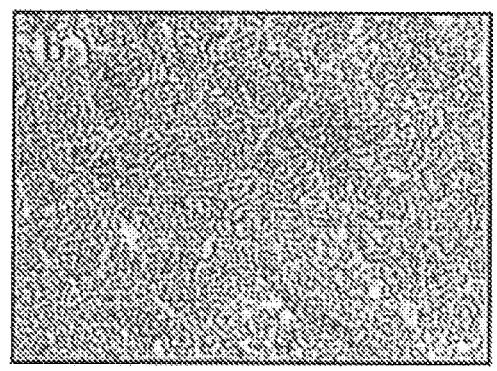
FIG. 3C    FIG. 3D
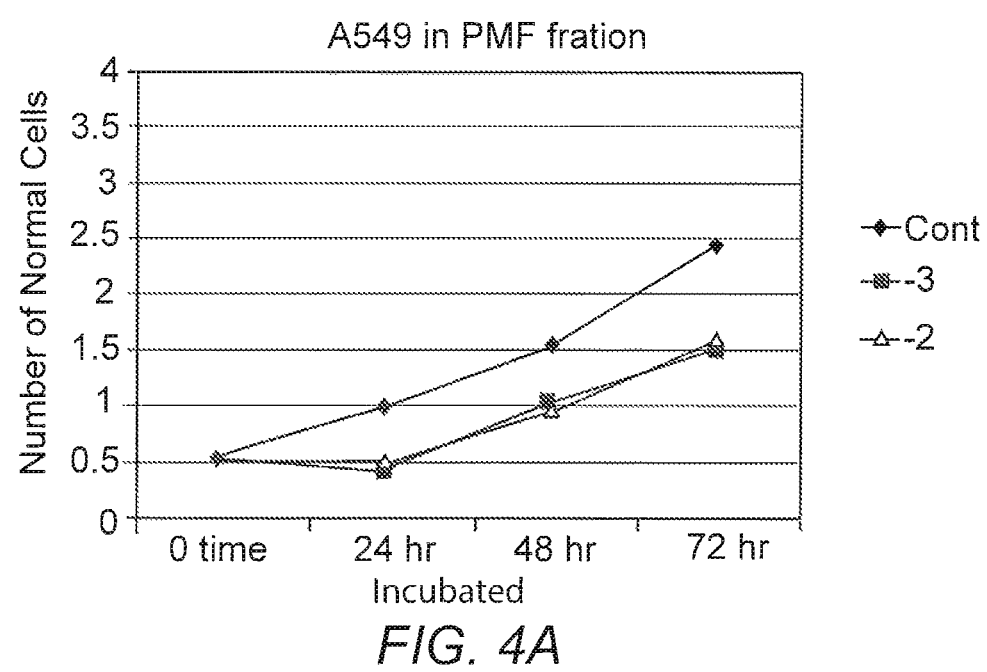
FIG. 4A 5g of Lyophilized PM701 was sonicated with methanol 3 times each 30 ml give 750 mg of methanol fraction (Fraction G), later called PMF PMF (1.5) was chromatogrpahed on Sitica gel column and was cluled with following solvents systems each 750 ml chloroform, 10% methanol in chloroform, 20% methanol in choloroform, 30% methanol in cholorform, 40% methanol in chloroform, 60% methanol in chloroform followed with methanol.

Seven subfractions (G1, G2, G3, G4, G5, G6 and G7)
G7, later called PMFK

FIG. 9

SEPARATION AND FORMULATION OF BIOACTIVE FRACTION AND SUBFRACTION FROM CAMEL URINE WORKS AS ANTICANCER AGENT

RELATED APPLICATIONS

This application is a divisional of application Ser. No. 12/178,152 filed Jul. 23, 2008, which claims priority from GCC Patent No. 9962 filed Jan. 1, 2008, both incorporated by reference in their entireties.

BACKGROUND OF THE INVENTION

1. Field of the Invention

The present invention relates to an absolutely novel use of camel urine for medicinal purposes and also relates to the preparation of it by lyophilization as a drug that called PM701 or fractionating it to active fractions that are coded as PMF and PMFK. More specifically, the present invention relates to isolating the bio-active fraction PMF and the most effective subfraction PMFK from the lyophilized PM701 of the adult single-humped Arabian camel, species *Camelus dromedarius* and the absolutely novel use of these bio-active fractions as a selective anti-cancer agent. The fractionation will be implicated in reducing the dosage of the whole lyophilized urine and increasing its efficacy. The invention also relates to the preparation of a novel pharmaceutical composition (capsules) comprising an effective amount of the bio-active fraction PMF or the bioactive subfraction in a composition of 435 mg/capsule with a range 7 or 5 capsules/day respectively, which are targeted to the human cancer tissues through their anti-proliferative and apoptotic activities without harming the other normal tissues.

2. Description of the Related Art

Cancers are uncontrolled cell proliferations that result from the accumulation of genetic changes in cells endowed with proliferative potential. After a variable latency period during which they are clinically silent, the malignant cells progress to aggressive invasive and metastatic stages with tumor formation and wide-spread dissemination throughout the body.

Despite important advances in treatment, cancers still account for 28% of death in Western countries, and more than this ratio in other countries. Treatment of cancer has relied mainly on surgery, chemotherapy, radiotherapy and more recently immunotherapy. However, for the most frequent types of cancers (lung, breast, colo-rectal and the leukemias) complete remission and cure has not been achieved. Therefore, the development of new approaches for treating cancer patients is highly desirable and critically needed particularly for those patients whose disease has progressed to a metastatic stage and are refractory to standard chemotherapy.

The world health organization published that cancer is a leading cause of death worldwide. From a total of 58 million deaths worldwide in 2005, cancer accounts for 7.6 million (or 13%) of all deaths, in 2005 cancer killed approximately 12,000 people in Saudi Arabia, as shown in FIG. 1, with 8,000 of those people were under the age of 70.

In Prophet Mohamned Medicine (peace be upon him), camel urine is suggested for drinking to improve some symptoms mainly associated with tumor formation in the body. Therefore, camel urine has been used in the Islamic and Arab world, sold and distributed in different size bottles. But it is never scientifically tested. The applicant considered it is worthwhile to scientifically look at this and define its value through in vitro and in vivo assays. The applicant has developed the curiosity about it and asked a number of questions: What possible importance can camel urine have? Whether the component camel urine is having any activity on tumor formation by itself or some of its parts? Does the fresh urine have any effects on human cancer tissues? Could one formulate this urine in a convenience form for human use? Does the formulation of urine enhance its activity or reduce it? Dose the camel urine contain microorganism? Is it safe to use it as a drug or does it have toxicological effects on human diverse organs?

In addition, could one fractionate the lyophilized camel urine in order to separate the bio-active fractions? To which part of the cell does the camel urine react? What are the biochemical, biophysical, and biological evidences for its efficacy?

Camel's urine can be considered as an effective animal origin substance/secretion with the capacity of improvement of some symptoms mainly associated with tumors formation in the body but it does need substantiation through scientific experimentation. Thus, the applicant considered it worthwhile to scientifically look at this and define its values through in vitro and in vivo assays. The applicant in the first instance probed whether it contained anti-cancer agent since such a property would make it a highly useful natural substance. In related art, use of 'piperine' as a bioavailability enhancer has been described in U.S. Pat. Nos. 5,616,593 and 5,972,382. Also cow's urine distillate or a dried fraction used for improving activity and bioavailability of antibiotics drugs as described in later U.S. Pat. No. 6,896,907.

BRIEF SUMMARY OF THE INVENTION

Some of the above questions have been solved and addressed herein. To answer the first set of questions the applicant collected the camel urine (PM701) from natural pastures in various areas within Jeddah, Makah, Madinah and Riyadh governorate (Saudi Arabia) in different size bottles at any time of the day. The urine was tested on CLED media and blood agar in sterile condition and did not notice any growth of microorganism. Tissue cultures of human cancer tissues and normal tissues were used in studying the effect of (camel urine) PM701 on the behavior of cancer cells and normal cells. PM701 appears to target the cancer cells and have anti-proliferative, apoptotic efficacy on them.

Surprisingly, the same PM701 exhibited nourishing effects on normal healthy cells; this implies that PM701 have a selectively killing effect on cancer cells and reparative effect on normal dividing cells, these results leading to this invention. The novelty of the invention lies in the fact revealed through precise experimentation that the PM701 action and its effectiveness are achievable only in the range of concentration which is literally in nano to micro-gram levels. That should be the reason for detection such a valuable potential of PM701 in targeted to the cancer cells. The utilized of fresh PM701 remains non-acceptable and non-convenience for human use therefore, the applicant also further lyophilized the liquid PM701 to obtain 0.2 g/ml of powder, we re-examined the lyophilized PM701 on normal cells and diverse cancer cells in both cell culture and animal models, which showed the same anti-cancer efficacy and that was mediated by apoptosis as determined by an MTT test and electron microscopy examination.

The applicant thought of utilizing PM701 as an alternative drug for cancer therapy since it showed a target effect on cancer cells and no side effects on the normal tissues, but the amount of lyophilized PM701 dosage per day was as a load in the body (46 capsules/day), ultimately leading to use one of the ways, which has been feasible for drastically reducing the daily dosage of this anti-cancer agent PM701 and increasing the efficiency of the dosage activity too and has also high commercial importance. Therefore the bio-guided fractionation approach was used with lyophilized PM701, which lead us to the isolation and identification of the bio-active fractions, which is responsible for the anti-cancer efficacy observed with the whole urine.

For the purpose of the present invention the following terms are defined below.

The term "anti-cancer therapy" is intended to mean growth inhibition/eradication of primary tumors, stabilization of tumor growth, inhibition of metastasis formation, or prevention of tumor formation. Furthermore, anticancer activity also covers any combination between our substances and other known or investigational anticancer agents, in order to improve the therapeutic efficacy of drugs.

The main purpose of this work is to reach an optimum alternative drug for cancer treatment other than radiation or chemotherapy.

A mainstream approach is treating cancer with new methods other than chemotherapy and radiotherapy, which have very bad side effects on normal tissues.

Another objective of the invention is to provide new use of the PM701 as a selective anti-cancer agent.

In another objective of the invention is to provide a method for improving activity of PM701 via its bio-active fractions.

Also another objective of the invention is to provide a process for the isolation of the active fractions form PM701 of camel urine.

Still another objective of the invention is to provide the bio-active fractions of lyophilized PM701 as in an effective amount as a novel pharmaceutical composition (capsules).

The important objective of the invention is to prevent destruction of normal tissues during the process of cancer treatment.

To reach a protocol for treating cancer patients with available substances and at a low cost.

The invention relates to a new use of known abundantly available camel urine as anti-cancer agent and to provide the bio-active fractions of it that be useful in cancer treatment. In accordance with one aspect of the invention there is provided a novel anti-cancer pharmaceutical composition comprising an acceptable, effective anti-cancer amount of bio-active fractions of PM701. The invented bio-active fractions targeted the cancer tissues without any side effects on the normal tissues.

BRIEF DESCRIPTION OF THE SEVERAL VIEWS OF THE DRAWINGS

FIG. 3C illustrates the in vitro cytotoxic effect of lyophilized PM701 using human lung carcinoma cell line, A549.

FIG. 9 illustrates schematically the process of fractionation and subfractionation of PM701.

DETAILED DESCRIPTION OF THE INVENTION

Figure 1:
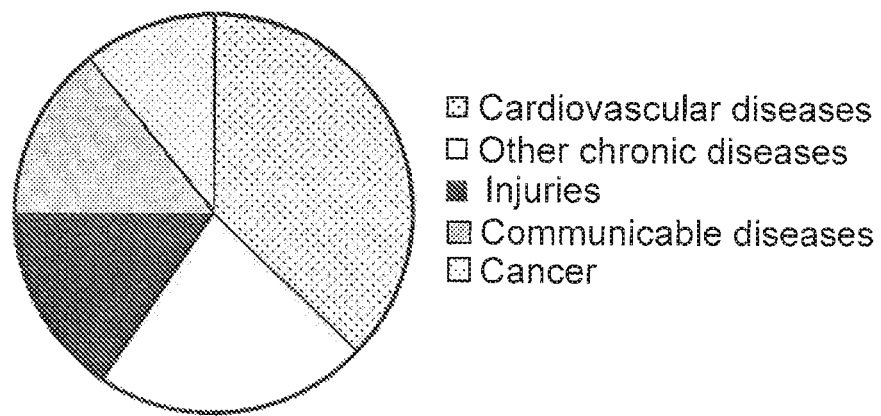
FIG. 1 is a chart of projected causes of death in Saudi Arabia.

As shown in FIGS. 2-9, the present invention solves the problem of searching for and obtaining a plentifully, available, cheap, and natural material (PM701) as an anti-cancer agent with a higher and selective potency on cancer cells, obtained from camel urine. Additionally, the bio-active fraction of PM701 was isolated, which is coded PMF due to its highly selectively and highly cytotoxic properties on cancer cells, which is responsible on the whole PM701 effect. Furthermore, PMF was subfractionated and led to purification of seven subfractions, the seventh which is coded PMFK has cytotoxic properties on cancer cells as much as PMF cytotoxic properties.

PMF and PMFK have cytotoxic and killing activities in vitro on human lung cancer cell line (A549) and mice leukemic cancer cell line (L1210) without affecting normal human foreskin cells HFS. More important were the obvious effects on inhibition the cancer cell division activity through the morphological hallmarks and biochemical features that characterize apoptosis, as shown by loss of cell viability, chromatin condensation, and reducing metabolic activity using an MTT test.

In another embodiment, PM701 was used in vivo in treating animal models that were inoculated with cancer cells; the result of in vivo testing is as satisfactory as in vitro effect at tissue culture level.

In an embodiment of the present invention a pharmaceutical composition comprising an effective amount of PMF or PMFK as bioactive anticancer compounds and pharmaceutically acceptable additives selected from anticancer compounds.

In another embodiment, PMF and PMFK are used as bioavailability anticancer therapy directly or in combination with other anticancer molecules.

In yet another embodiment, PMF and PMFK are induced the apoptosis of cancer cells.

In yet another embodiment, the PM701 fractionation helps us to isolate the bio-active molecules, which act better on the target cancer cells by decreasing its proliferation.

In yet another embodiment, the cancer cells may be lung, leukemia or any cancer cells.

In yet another embodiment, PMF used in vitro in the range between 80 µg/ml to 800 µg/ml and PMFK used in the range between 0.2 µg/ml to 2 µg/ml.

In still another embodiment, the bioactive fractions (PMF and PMFK) enhance the antiproliferative and apoptotic activities of anti-cancer agents (PM701) for 2.8 folds.

The methodology followed by us for this screening included specifically designed in vitro and in vivo bioassays as described below. The cell lines used in this invention were obtained from cell bank of Tissue Culture Unit in King Fahd Medical Research Center (KFMRC).

Development of Powder Form

For enhancing the utility and convenience of application of PM701, liquid PM701 was lyophilized to reach a solid form. The applicant further fractionated the solid form to obtain the bioactive fraction(s), which is also free of the typical smell of camel urine that it is more readily acceptable to the humans. For this purpose the lyophilized PM701 was fractionated as described by the following procedure:

Step 1: PM701 was collected in the stainless steel container directly from the camel, which is maintained in hygienic environment.

Step 2: 90 gm of liquid PM701 was added to Microcrystalline cellulose (10 gm). This will give 100 gm of a mixture, that frozen at −80° C. in Pyrex apparatus for 20-24 hrs.

Steps 3: 100 gm of the mixture is lyophilized in the lyophilizer at room temperature for 5 days to obtain 20 gm of solid form PM701.

Step 4: Mixtures leave in a desiccator with calcium chloride, in present of vacuum pressure for one day at room temperature.

Step 5: The lyophilized PM701 is packed in fridge in a sterilized glass container for further use.

Fractionation of a Lyophilized PM701 Separation of Active Ingredients

The following steps were performed.
i. Solvent Extraction Method for Fractionation
Step 1: A sample of 5 mg of lyophilized PM701 was sonicated with methanol three times each 30 ml to give about 750 mg of methanol fraction, which is called (PMF).

ii. Molecular Sieving Method for Subfractionation
Step 1: Subfractionation of PMF using column of different type of gel with different sieving capacity (e.g. Sephadex LH-20, Sephadex-25, -50, . . . ).

Step 2: A sample of 1.5 mg of The methanol fraction (PMF) was chromatographed on Silica gel column and was eluted with following solvents systems each 250 ml, chloroform, 10% methanol in chloroform, 20% methanol in chloroform, 30% methanol in chloroform, 40% methanol in chloroform, 60% methanol in chloroform followed with methanol.

Step 3: The seven subfractions are purified and individual sub fractions are separated by high-performance liquid chromatography.

Step 4: All subfractions, which comes out of column were tested for similar activity as that of PM701 at the tissue culture level.

Figure 2:
FIG. 2 illustrates the chromatographic subfractionation of the organic soluble fraction PMF (G) led to the isolation of 7 subfractions referred to as G1-G7.

The organic solvent soluble fractions and subfractions were found to have a strong antiproliferative activity in a panel of human cancer cell lines derived from lung and leukemia. In vitro, the fractions and subfractions demonstrate antiproliferative and antiapoptotic activities in tissue culture experiments, as shown in FIGS. 2 and 9.

Assay for In Vitro Dose Determination a. The optimum inhibitory concentration of PM701 is evaluated and determined against different cancer cells, human lung cancer cell line (A549), leukemic cell line (L1012) through the in vitro tissue culture experiments.

b. The optimum inhibitory concentration of PM701 showing a cytotoxic effect on cancer cells while there is no any cytotoxic effect on normal cells, suggesting that PM701 can act selectively on cancer cells while nourishing normal cells.

1 ml dissolved PM701 or PMF or PMFK in 10 ml standard media, which is called −1 (high).

1 ml dissolved PM701 or PMF or PMFK in 100 ml standard media, which is called −2.

1 ml dissolved PM701 or PMF or PMFK in 1,000 ml standard media, which is called −3 (mid).

1 ml dissolved PM701 or PMF or PMFK in 10,000 ml standard media, which is called −4.

1 ml dissolved PM701 or PMF or PMFK in 100,000 ml standard media, which is called −5 (low).

The in vitro experiments showed that the best effect observed when used mid −2 and −3 concentrations, so we fixed the in vitro and in vivo doses using these medium concentration.

In Vitro Antiproliferative Activity Assay (Cell Culture)

Cell Lines and Cell Culture
1. Lung cancer (A549) commercial cell line obtained from King Fahd Medical Research Center (KFMRC) is inoculated at a density of about $0.5 \times 10^5$ cells in MEM medium in the wells of 24 well plate. L1210 cells were prepared by the same way in RPMI (1640) supplemented with 10% heat-inactivated fetal calf serum.

2. This is replaced with fresh medium after 24 hours in each well.

3. The test component(s) is added at desired concentrations in different wells just after the medium replacement.

4. Observations are recorded on the cell count after 0, 24, 48, and 72 hours for which the following steps are required.

a. The medium is removed from the wells.

b. The wells are rinsed with 1 ml PBS (Phosphate buffer saline).

c. To each well 500 µl of freshly prepared trypsin (0.1% in PBS) solution is added.

d. Typsin solution is removed after 30 seconds and the plate is gently tapped till the cells are released from the plate surface.

e. Fresh 1 ml of growth medium is added and agitated with a pipette to obtain a cell suspension.

f. Cell suspension was prepared (1:1): 20 ml of cells with 20 ml of (0.4%) Trypan blue, 10 µl of cell suspension is taken on the haemocytometer and a cover glass is placed over the counting chamber.

g. The number of viable cells is counted in 5 big squares and the readings are taken from 5 microscopic fields to determine the average.

h. The cell count (titer per ml) in the original sample is then calculated as average count×$10^4$.

Composition of Minimum Essential Medium (MEM)

MEM powder (ICN)=9.95 g, $NaHCO_3$(Powder)=2.2 g, glutamine (Powder)=0.3 g L, Non essential amino acid (100×)=10 ml, Hepes (100×) solution=10 ml, antibiotic mix (Penicillin+Streptomycin)=10 ml, deionzed-distilled water=1 liter.

Stirrer for 1 hrs at room temperature, PH (6.8-7.4).

Sterile-filtered through a 0.22 µm filter and stored at +4'C.

Figure 3A:
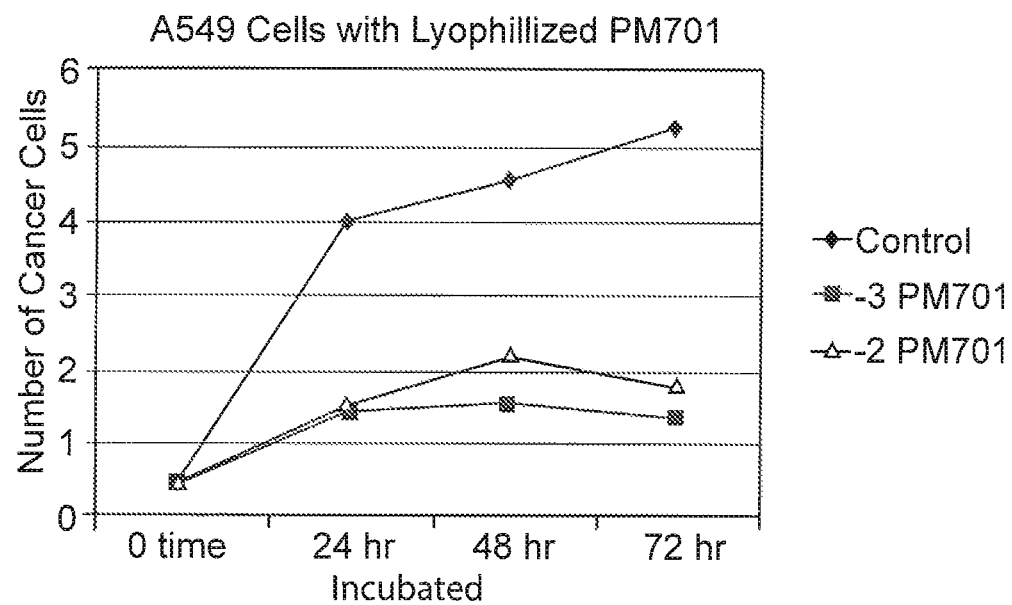
FIG. 3A illustrates a curve of the in vitro cytotoxic effect of lyophilized PM701 using human lung carcinoma cell line, A549 in different incubated periods comparing with non treated cancer cells.

FIG. 3A illustrates a curve of the in vitro cytotoxic effect of lyophilized PM701 using human lung carcinoma cell line, A549 in different incubated periods comparing with non treated cancer cells.

Figure 3B:
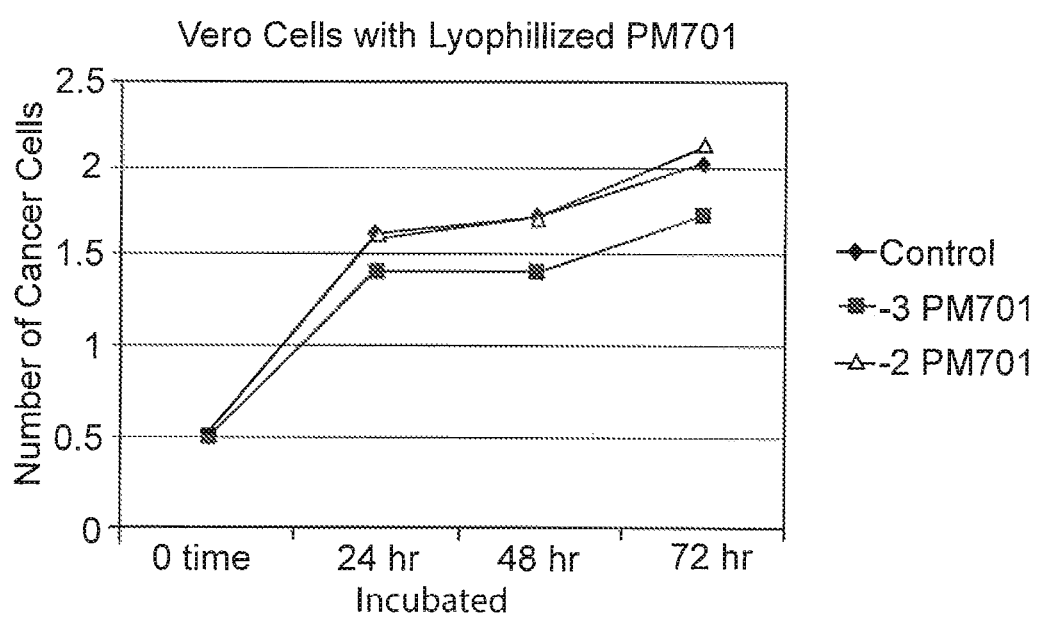
FIG. 3B illustrates a curve of the in vitro non-cytotoxic effect of lyophilized PM701 using human foreskin cell line, HFS in different incubated periods comparing with non treated normal cells.

FIG. 3B illustrates a curve of the in vitro non-cytotoxic effect of lyophilized PM701 using vero cell line in different incubated periods comparing with non treated normal cells.

FIG. 3C illustrates the effect of lyophilized PM701 on the cell morphology of human lung carcinoma cell line, A549. Cancer cells A549 imaged (40×) after incubation for 24 h, fixed and stained with Coomassie blue (a) in PM 701. Note the damage of cells as compared with the control cells that were incubated in MEM media (b).

FIG. 4A illustrates a curve of the in vitro cytotoxic effect of PMF fraction using human lung carcinoma cell line, A549 in different incubated periods comparing with non treated cancer cells.

Figure 4B:
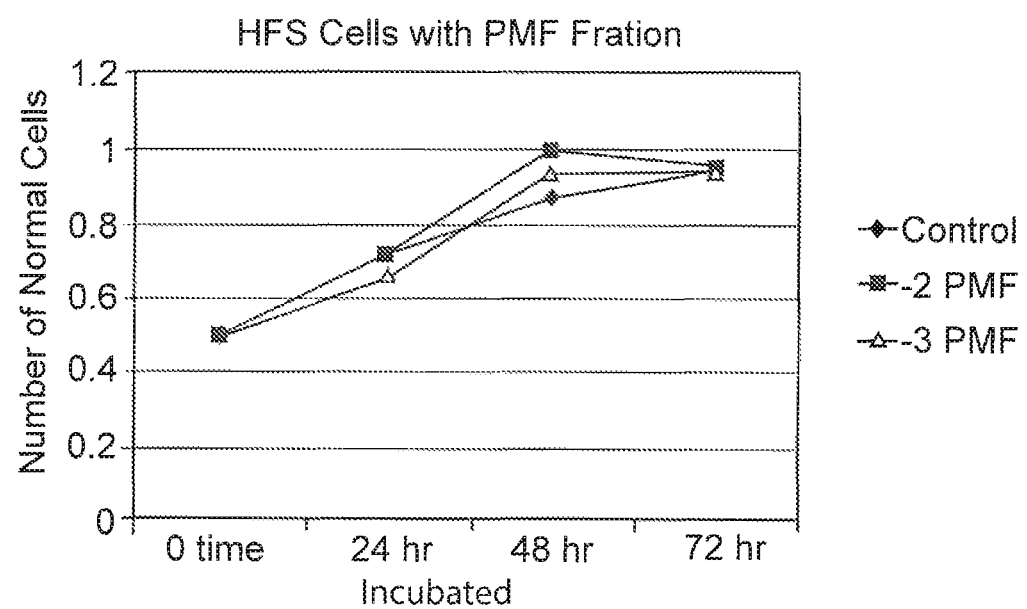
FIG. 4B illustrates a curve of the in vitro non-cytotoxic effect of PMF fraction using normal human foreskin cell line, HFS in different incubated periods comparing with non treated normal cells.

FIG. 4B illustrates a curve of the in vitro non-cytotoxic effect of PMF fraction using human foreskin cell line, HFS in different incubated periods comparing with non treated normal cells.

Figure 4C:
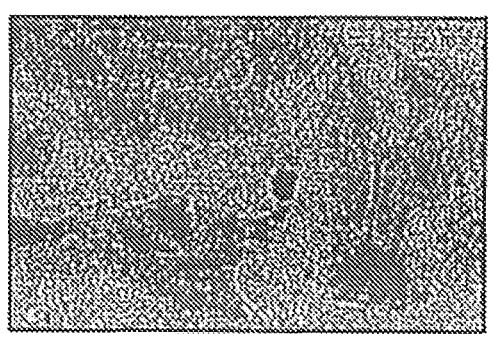
FIG. 4C illustrates the in vitro cytotoxic effect of PMF fraction using human lung carcinoma cell line, A549.
Figure 4D:
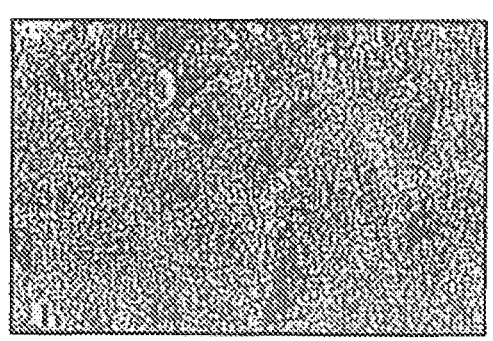
FIG. 4A illustrates curve of the in vitro cytotoxic effect of PMF fraction using human lung carcinoma cell line, A549 in different incubated periods comparing with non treated cancer cells.

FIG. 4C illustrates the effect of PMF fraction on the cell morphology of human lung carcinoma cell line, A549, a. treated cells; b. non treated cells (40×).

Figure 5A:
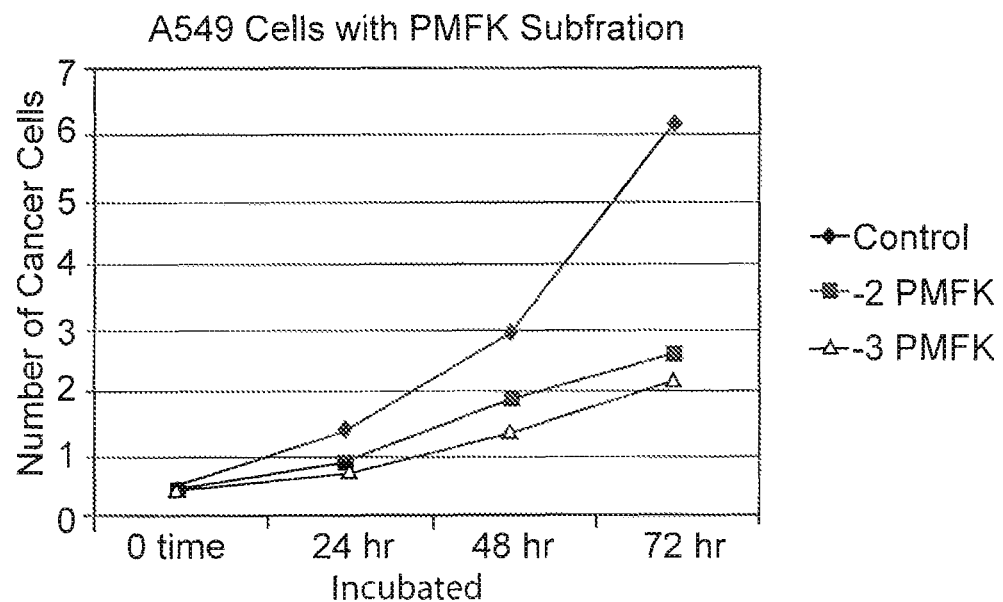
FIG. 5A illustrates a curve of the in vitro cytotoxic effect of PMFK subfraction using human lung carcinoma cell line, A549 in different incubated periods comparing with non treated cancer cells.

FIG. 5A illustrates a curve of the in vitro cytotoxic effect of PMFK subfraction using human lung carcinoma cell line, A549 in different incubated periods comparing with non treated cancer cells.

Figure 5B:
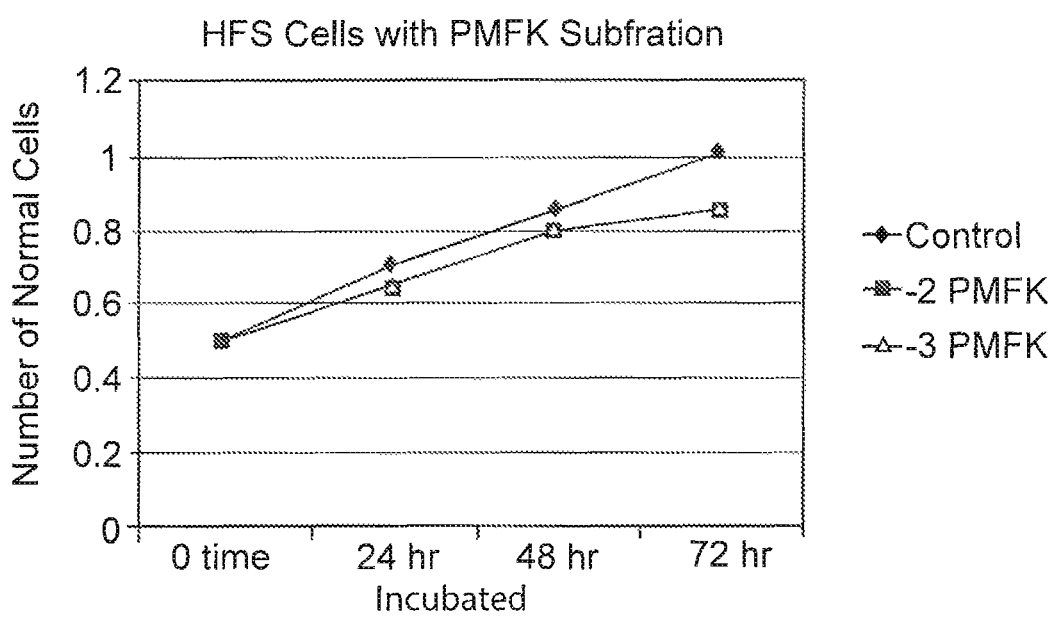
FIG. 5B illustrates a curve of the in vitro non-cytotoxic effect of PMFK subfraction using normal human foreskin cell line, HFS in different incubated periods comparing with non treated normal cells.

FIG. 5B illustrates a curve of the in vitro non-cytotoxic effect of PMFK subfraction using human foreskin cell line, HFS in different incubated periods comparing with non treated normal cells.

Figure 5C:
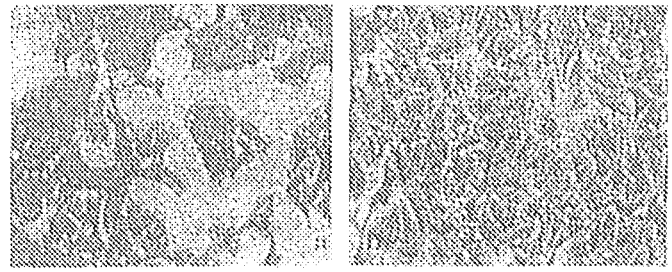
FIG. 5C illustrates the in vitro cytotoxic effect of PMFK subfraction using human lung carcinoma cell line, A549.

FIG. 5C illustrates the effect of PMFK subfraction on the cell morphology of human lung carcinoma cell line, A549, a. treated cells; b. non treated cells (20×).

Figures 6A, 6B:
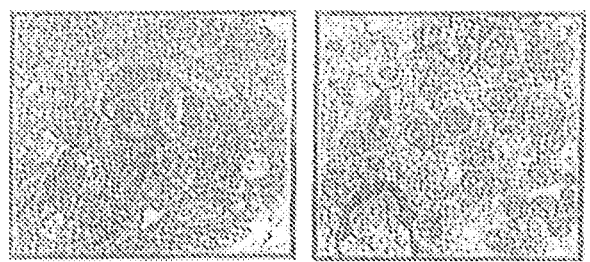
FIG. 6 illustrates ultrastructural morphological hallmarks features that characterize apoptosis, as shown by chromatin condensation and membrane blebbing in treated cancer cells with PM7011.
Figure 7A:
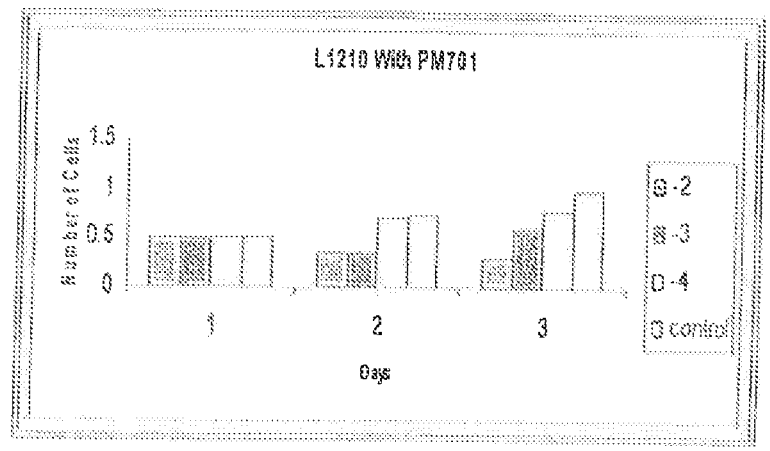
FIG. 7A illustrates the in vitro cytotoxic effect of the −2, −3, and −4 concentration of PM701 using mice leukemia cells, L1210.
Figure 7B:
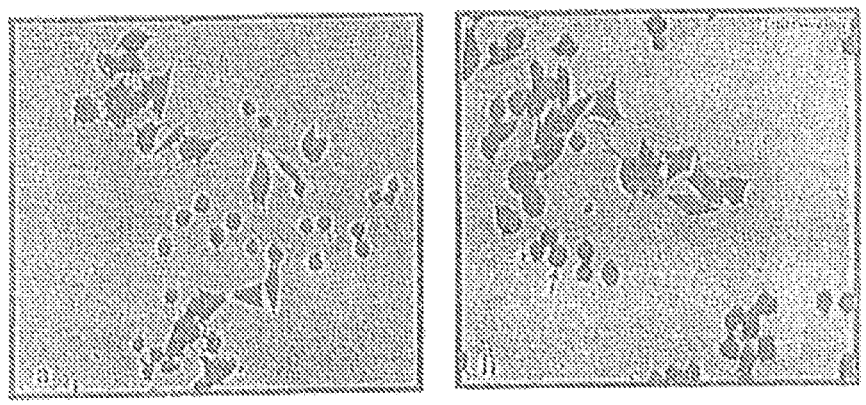
FIG. 7B illustrates the effect of PM 701 on the cell morphology of mice leukemia cells, L1210, a—treated cells; b—non-treated cells—note the normal cell size (arrows) (40×).

FIG. 6 illustrates ultrastructural morphological hallmarks features that characterize apoptosis, as shown by chromatin condensation and membrane blebbing in treated cells with PM701.

Cytotoxicity Assay

The MTT test is used for determination of the cytotoxicity or the anticarcinogenic effects of PM701 on two types of cancer cells, A549 and L1210. This test measures the cell viability as a percentage of control untreated cells.

An MTT assay was performed to evaluate the growth effects of PM 701. The MTT assay is colorimetric assay based on the tetrazolium salt MTT that detects cell viability. Dissolved MTT is converted to an insoluble purple formazan by cleavage of the tetrazolium ring by dehydrogenase enzymes in living but not dead cells.

MTT was dissolved in phosphate buffered saline (PBS) at 5 mg/ml and filtered through a 0.22 µm filter to sterilize and remove the small amount of insoluble residue then stored at 2-8° C. for frequent use. Stock solution of MIT is added to each culture being assayed to equal one tenth the original culture volume.

Using isopropanol is measured by spectrophotometricaly yielding absorbance as a function of concentration of converted dye.

Exponentially growing cells ($3\times10^3$ cells/100 µl) were seeded in 96-well plates and incubated for 24 h. Cells were then treated continuously with the various fractions and subtractions. At a selected time, 10 µl of stock MTT solution was added to all wells for the assay. After a further period of incubation (4 hours), the medium was aspirated from the wells as completely as possible without disturbing the formazan crystals. Then, 100 µl of isopropanol is added to each well for dissolving the resulting precipitate. The concentration of the dye is then measured at 570 nm on plate reader (Microplate Reader Model 450; Bio-Rad). The optical density obtained is directly related to the viability of cells.

The MTT assay distinguishes between viable and non-viable cells on the basis that physiologically active mitochondria metabolizes the MTT only in viable cells. The IC50 was calculated as the concentration of drug causing a 50% inhibition in the absorbance compared to cells treated with solvent alone.

Figure 8A:
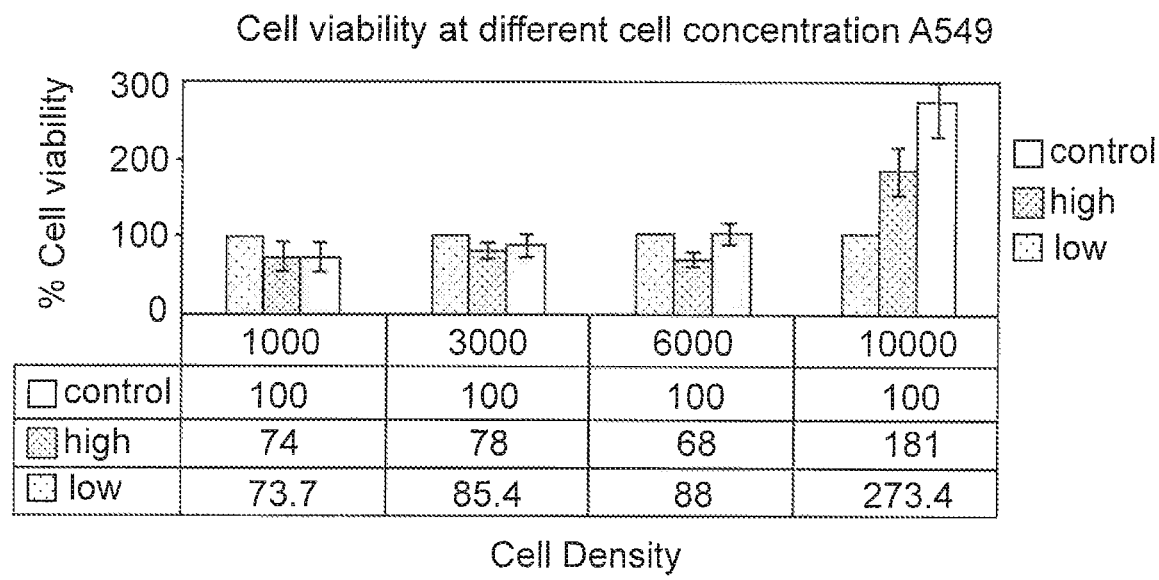
FIG. 8A illustrates an MTT test show the effect of two different concentrations of PM701: −2 or high and −3 or low on four different cell densities 1, 3, 6 and $10 \times 10^3$ cell/well.

FIG. 8A illustrates an MTT test show the effect of two different concentrations of PM701: −2 or high and −3 or low on four different cell densities 1, 3, 6 and 10×103 cell/well.

Figure 8B:
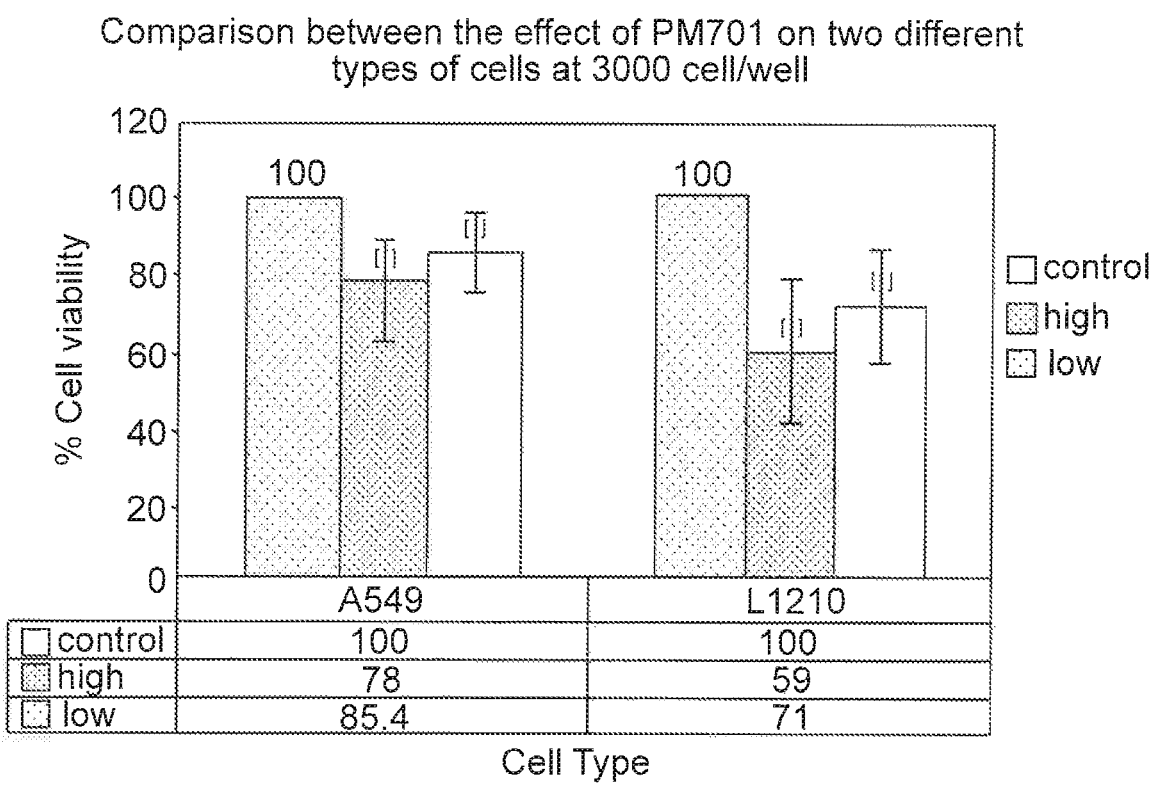
FIG. 8B illustrates an MTT test shows the effect of PM701 on two types of carcinogenic cells A549 and L1210 at $3 \times 10^3$ cell/well.

FIG. 8B illustrates an MTT test shows the effect of PM701 on two types of carcinogenic cells A549 and L1210 at 3×103/well.

Results

Methanol soluble fraction (PMF) but not water soluble fractions, was found to have a potent antiproliferative activity in A549 and L1210 cell lines. Further chromatographic subfractionation of these organic soluble extract led to the isolation of 7 fractions referred to as G1-G7, as shown in FIG. 2 which illustrates the chromatographic subfractionation of the organic soluble fraction PMF led to the isolation of 7 subfractions referred to as G1-G7. Solvent system: CHCl3-MeOH-Water 65:35:6. Spray Reagent: P-anisaldehyde Reagent. Heating at 110° C. for 5 min.

PM701, PMF, and PMFK showed highly cytotoxic effect on cancer cells compared with non-cytotoxic effect on normal cells.

FIG. 3A illustrates a curve of the in vitro cytotoxic effect of lyophilized PM701 using human lung carcinoma cell line, A549 in different incubated periods comparing with non-treated cancer cells.

FIG. 3B illustrates a curve of the in vitro non-cytotoxic effect of lyophilized PM701 using vero cell line in different incubation periods comparing with non-treated normal cells.

FIG. 3C illustrates the effect of lyophilized PM701 on the cell morphology of human lung carcinoma cell line, A549. Cancer cells A549 imaged (40×) after incubation for 24 h, fixed and stained with Coomassie blue (a) in PM701. Note the damage of cells as compared with the control cells that were incubated in MEM media (b).

FIG. 4A illustrates a curve of the in vitro cytotoxic effect of PMF fraction using human lung carcinoma cell line, A549 in different incubated periods comparing with non treated cancer cells.

FIG. 4B illustrates a curve of the in vitro non-cytotoxic effect of PMF fraction using human foreskin cell line, HFS in different incubated periods comparing with non-treated normal cells.

FIG. 4C illustrates the in vitro cytotoxic effect of PMF fraction using human lung carcinoma cell line, A549, a. treated cells; b. non-treated cells (40×).

FIG. 5A illustrates a curve of the in vitro cytotoxic effect of PMFK subfraction using human lung carcinoma cell line, A549 in different incubated periods comparing with no-treated cancer cells.

FIG. 5B illustrates a curve of the in vitro non-cytotoxic effect of PMFK subfraction using human foreskin cell line, HFS in different incubated periods comparing with non-treated normal cells.

FIG. 5C illustrates the in vitro cytotoxic effect of PMFK subfraction using human lung carcinoma cell line, A549, a. treated cells; b. non-treated cells (20×).

The morphological changes of treated cells with lyophilized PM701 characterize apoptosis, as shown by loss of cell viability, membrane blebbing, and chromatin condensation and shown in FIG. 6.

FM701 reduced metabolic activity of cancer cells using MTT test as shown in FIGS. 8A and 8B. More particularly, FIG. 8A illustrates an MTT test show the effect of two different concentrations of PM701: −2 or high and −3 or low on four different cell densities 1, 3, 6 and 10×10$^3$ cell/well. FIG. 8B illustrates an MTT test shows the effect of PM701 on two types of carcinogenic cells A549 and L1210 at 3×10$^3$/well.

Methanol soluble fraction PMF was found to have a good anticancer activity carcinoma cell lines. A dose relationship was also observed, as shown in FIG. 4A.

Alternative Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

Still more interesting observation is that the in vivo study on the animal models, which indicated that (PM 701) has the ability to limit cancer progression in treated animals by at least 3 folds, which means that it has a favorable antimitotic effect. Further patent in this direction have been in progress.

What is claimed is:

1. A method for treating lung cancer or leukemia in a human patient comprising administering to said human patient with lung cancer or leukemia an effective amount of a fractionate of camel urine to treat the lung cancer or leukemia, said fractionate of camel urine obtained by:
   (i) lyophilizing a sample of camel urine to obtain a lyophilisate;
   (ii) sonicating a sample of said lyophilisate with methanol, to secure a methanol fractionate;
   (iii) subjecting said methanol fractionate to silica gel chromatography; and
   (iv) eluting said methanol fractionate with a solvent system consisting of chloroform or chloroform and methanol.

2. The method of claim 1, wherein said cancer is lung cancer.

3. The method of claim 1, wherein said cancer is leukemia.

4. The method of claim 1, wherein said solvent system consists of 10% methanol in chloroform, 20% methanol in chloroform, 30% methanol in chloroform, 40% methanol in chloroform, or 60% methanol in chloroform followed by methanol.

5. The method of claim 1, wherein said fractionate further comprises a pharmaceutically acceptable carrier.

6. The method of claim 1, wherein said camel is a single humped, Arabian camel (*Camelus dromedaries*).

7. The method of claim 1, wherein said fractionate has been lyophilized with microcrystalline cellulose.

* * * * *